(12) United States Patent
Werbickas

(10) Patent No.: US 9,498,580 B2
(45) Date of Patent: Nov. 22, 2016

(54) HYPODERMIC SYRINGE APPARATUS HAVING A NEEDLE GUARD ASSEMBLY WITH SHIELDING FOR PROTECTION FROM THE NEEDLE AFTER USE

(71) Applicant: Alexander Werbickas, Marlton, NJ (US)

(72) Inventor: Alexander Werbickas, Marlton, NJ (US)

( * ) Notice: Subject to any disclaimer, the term of this patent is extended or adjusted under 35 U.S.C. 154(b) by 384 days.

(21) Appl. No.: 13/986,102

(22) Filed: Apr. 1, 2013

(65) Prior Publication Data

US 2013/0261559 A1 Oct. 3, 2013

Related U.S. Application Data

(60) Provisional application No. 61/686,297, filed on Apr. 3, 2012.

(51) Int. Cl.
*A61M 5/32* (2006.01)
(52) U.S. Cl.
CPC ......... *A61M 5/3245* (2013.01); *A61M 5/3257* (2013.01)
(58) Field of Classification Search
CPC ............ A61M 5/321; A61M 5/3243; A61M 5/3245; A61M 5/3257; A61M 5/3269; A61M 5/3271; A61M 5/3273; A61M 5/3275; A61M 2005/3246; A61M 2005/3247; A61M 2005/3258
USPC ........................................ 604/187, 192, 198
See application file for complete search history.

(56) References Cited

U.S. PATENT DOCUMENTS

| | | |
|---|---|---|
| 2,857,912 A | 10/1958 | Feinstone et al. |
| 4,659,330 A | 4/1987 | Nelson et al. |
| 4,693,708 A | 9/1987 | Wanderer et al. |
| 4,735,617 A | 4/1988 | Nelson et al. |
| 4,826,488 A | 5/1989 | Nelson et al. |
| 4,894,055 A | 1/1990 | Sudnak |
| 4,897,083 A | 1/1990 | Martell |
| 4,911,693 A | 3/1990 | Paris |
| 4,976,702 A | 12/1990 | Andrews et al. |
| 4,994,046 A | 2/1991 | Wesson et al. |
| 5,011,475 A | 4/1991 | Olson |
| 5,026,345 A | 6/1991 | Teringo |
| 5,057,089 A | 10/1991 | Greco |
| 5,098,403 A | 3/1992 | Sampson |
| 5,151,090 A | 9/1992 | Best et al. |
| 5,195,983 A | 3/1993 | Boese |
| 5,215,535 A | 6/1993 | Gettig et al. |
| 5,219,338 A | 6/1993 | Haworth |
| 5,267,972 A | 12/1993 | Anderson |
| 5,334,155 A | 8/1994 | Sobel |
| 5,401,246 A * | 3/1995 | Mazur et al. ................. 604/110 |
| 5,429,612 A | 7/1995 | Berthier |

(Continued)

*Primary Examiner* — Quynh-Nhu H Vu
(74) *Attorney, Agent, or Firm* — Fox Rothschild LLP

(57) ABSTRACT

The present invention provides a novel construction for a hypodermic syringe apparatus by the inclusion of a needle guard assembly with shielding for protection of the needle after use and preventing of the spreading of disease and/or infection to users or localized personnel prior to disposal of the disposable syringe. The assembly includes a needle cover which is preferably tubular and is movable between a retracted positioned within the syringe and a deployed position extending around the needle for preventing contact therewith. A unique locking mechanism is included with two pins and two unlocking buttons for selectively initiating unlocking of the needle cover to facilitate movement of it to the deployed position responsive to activation of a needle cover button.

21 Claims, 13 Drawing Sheets

(56) References Cited

U.S. PATENT DOCUMENTS

| | | |
|---|---|---|
| 5,431,630 A | 7/1995 | Leonard |
| 5,509,907 A | 4/1996 | Bevilacqua |
| 5,540,667 A | 7/1996 | Tanner, II |
| 5,817,064 A | 10/1998 | DeMarco et al. |
| 6,017,329 A | 1/2000 | Hake |
| 6,086,566 A | 7/2000 | Arnissolle |
| 6,149,630 A | 11/2000 | Robinson |
| 6,156,011 A | 12/2000 | Ruminson |
| 6,183,445 B1 | 2/2001 | Lund et al. |
| 6,398,762 B1 | 6/2002 | Vetter et al. |
| 6,454,746 B1 * | 9/2002 | Bydlon et al. ............... 604/227 |
| 6,537,257 B1 | 3/2003 | Wien |
| 6,976,976 B2 * | 12/2005 | Doyle .................. A61M 5/326 604/198 |
| 7,824,379 B2 | 11/2010 | Doyle |
| 7,875,006 B2 | 1/2011 | Pessin |
| 8,241,255 B2 | 8/2012 | Doyle |
| 2006/0036217 A1 * | 2/2006 | Doyle .................. A61M 5/326 604/198 |
| 2009/0326476 A1 * | 12/2009 | Carlyon ...................... 604/197 |

* cited by examiner

HYPODERMIC SYRINGE APPARATUS HAVING A NEEDLE GUARD ASSEMBLY WITH SHIELDING FOR PROTECTION FROM THE NEEDLE AFTER USE

The present utility application hereby formally claims priority of currently U.S. Provisional Patent application No. 61/686,297 filed Apr. 3, 2012 on "SAFETY SYRINGE CONSTRUCTION" filed by the same inventor listed herein, namely, Alexander Werbickas, and said referenced provisional application is hereby formally incorporated by reference as an integral part of the present application.

BACKGROUND OF THE INVENTION

The present invention relates to the field of healthcare and medical equipment, and in particular, to subcutaneous injection devices for the injection or removal of liquid, such as blood or the like from a human body utilizing a hypodermic syringe. Such needle devices are commonly disposable immediately after use to prevent any chances of infection or the spreading of any disease carried on the used needle. More particularly, the present invention applies to constructions for such hypodermic syringes such that the needle portion thereof is guarded or shielded in such a manner as to prevent contact with health care workers or others prior to disposal thereof.

DESCRIPTION OF THE PRIOR ART

Various patents have been granted on a means for shielding or protecting of the disposable hypodermic syringe after use thereof as shown in U.S. Pat. No. 2,857,912 issued Oct. 28, 1958 on a "Syringe Needle Protector" patented to T. Feinstone et al; and U.S. Pat. No. 4,659,330 issued Apr. 21, 1987 on a "Hypodermic Syringe Needle Guard" to Robert Nelson et al; and U.S. Pat. No. 4,693,708 issued Sep. 15, 1987 on a "Combination Needle Shield/Needle Guard Device for A Hypodermic Syringe With A Permanently Attached Needle" to Alan A. Wanderer et al; and U.S. Pat. No. 4,735,617 patented Apr. 5, 1988 on a "Hypodermic Syringe Needle Guard" to Robert A. Nelson et al; and U.S. Pat. No. 4,826,488 patented May 2, 1989 on a "Hypodermic Syringe Needle Guard" to Robert A. Nelson et al; and U.S. Pat. No. 4,894,055 patented Jan. 16, 1990 on a "Needle Guard Assembly For Use With Hypodermic Syringes And The Like" to Paul J. Sudnak; and U.S. Pat. No. 4,897,083 patented Jan. 30, 1990 to Michael D. Martell on a "Syringe Needle Guard"; and U.S. Pat. No. 4,911,693 patented Mar. 27, 1990 to Frassetti R. Paris on a "Hypodermic Syringe Needle Guard"; and U.S. Pat. No. 4,976,702 patented Dec. 11, 1990 to E. Trent Andrews et al on a "Syringe Needle Guard"; and U.S. Pat. No. 4,994,046 patented Feb. 19, 1991 to Vann T. Wesson et al and assigned to Vann T. Wesson on a "Needle Guard For Syringe"; and U.S. Pat. No. 5,011,475 patented Apr. 30, 1991 to Richard A. Olson on a "Protector For Intravenous And Syringe Needles"; and U.S. Pat. No. 5,026,345 patented Jun. 25, 1991 to William Teringo on a "Non-Mechanical Incapacitation Syringe Safety Needle Guard; and U.S. Pat. No. 5,057,089 patented Oct. 15, 1991 to Robert M. Greco on a "Syringe Needle Guard"; and U.S. Pat. No. 5,098,403 patented Mar. 24, 1992 to Edward J. Sampson and assigned to Infusaid Inc. on a "Universal Needle Guard"; and U.S. Pat. No. 5,151,090 patented Sep. 29, 1992 to Robert J. Best et al and assigned to Abbott Laboratories on a "Syringe And Needle Guard Assembly; and U.S. Pat. No. 5,195,983 patented Mar. 23, 1993 to Ted Boese and assigned to Penta Associates on a "Syringe Guard And Disposal System; and U.S. Pat. No. 5,215,535 patented Jun. 1, 1993 to William A. Gettig et al and assigned to Gettig Technologies Incorporated on a "Needle Protector Apparatus"; and U.S. Pat. No. 5,219,338 patented Jun. 15, 1993 to Warren D. Haworth on a "Safety Syringe With Collapsible Needle Guard; and U.S. Pat. No. 5,267,972 patented Dec. 7, 1993 to Wayne W. Anderson on a "Hypodermic Syringe With Needle Guard"; and U.S. Pat. No. 5,334,155 patented Aug. 2, 1994 to Daniel Sobel on a "Hypodermic Syringe Needle Guard"; and U.S. Pat. No. 5,429,612 patented Jul. 4, 1995 to Michael Berthier and assigned to Dentoptic on a "Syringe With A Slidable Needle Protection Device"; and U.S. Pat. No. 5,431,630 patented Jul. 11, 1995 to Robert J. Leonard and assigned to Surgic-Acid, Inc. on a "Needle Guard And Nonreusable Syringe"; and U.S. Pat. No. 5,509,907 patented Apr. 23, 1996 to Al Bevilacqua and assigned to Med-Safe Products, Inc. on a "Syringe Needle Guard Assembly; and U.S. Pat. No. 5,540,667 patented Jul. 30, 1996 to John C. Tanner, II and assigned to Abbott Laboratories on a "Needle Guard Assembly For Syringe"; and U.S. Pat. No. 5,817,064 patented Oct. 6, 1998 to Anthony O. DeMarco et al and assigned to American Home Products Corporation on a "Syringe Needle Guard"; and U.S. Pat. No. 6,017,329 patented Jan. 25, 2000 to Lawrence W. Hake on a "Hypodermic Needle Guard And Method To Prevent Needle Stick Injuries"; and U.S. Pat. No. 6,086,566 patented Jul. 11, 2000 to Yves Arnissolle and assigned to Societe d'Etudes et d'Applications Techniques-S.E.D.A.T. on an "Injection Syringe With Movable Needle Protector"; and U.S. Pat. No. 6,149,630 patented Nov. 21, 2000 to Phillip J. Robinson and assigned to Owens-Illinois Closure Inc. on a "Syringe With Squeeze Release Needle Guard"; and U.S. Pat. No. 6,156,011 patented Dec. 5, 2000 to Wallace E. Ruminson on a "Syringe Needle Guard"; and U.S. Pat. No. 6,183,445 patented Feb. 6, 2001 to Per William Lund, et al and assigned to Radiometer Medical A/S on a "Syringe With Retractable Needle Guard"; and U.S. Pat. No. 6,537,257 patented Mar. 25, 2003 to Abraham Wien on a "Syringe With Reciprocating, Leak-Proof Needle Guard"; and U.S. Pat. No. 6,398,762 patented Jun. 4, 2002 to Helmut Vetter et al and assigned to Arzneimittel GmbH Apotheker Vetter & Co. Ravensburg on a "Syringe Needle Protector"; and U.S. Pat. No. 6,976,976 patented Dec. 20, 2005 to Mark Christopher Doyle and assigned to Safety Syringes, Inc. on a "Syringe With Needle Guard Injection Device"; and U.S. Pat. No. 7,824,379 patented Nov. 2, 2010 to Mark Christopher Doyle and assigned to Safety Syringes, Inc. on a "Syringe With Needle Guard Injection Device"; and U.S. Pat. No. 7,875,006 patented Jan. 25, 2011 to Olivier Pessin and assigned to SEDAT of Irigny, (FR) on a "Needle Protection Device For A Syringe And An Injection Device Comprising A Syringe And Said Protection Device"; and U.S. Pat. No. 8,241,255 patented Aug. 14, 2012 to Mark Christopher Doyle and assigned to Safety Syringes, Inc. on a "Syringe With Needle Guard Injection Device".

SUMMARY OF THE INVENTION

A unique construction for a hypodermic syringe apparatus is shown in the present invention wherein a needle guard assembly is included which integrally includes a shielding for protection of the spread of disease from the needle or to prevent accidental injection of healthcare workers or other persons who may be handling the syringe apparatus prior to the disposal thereof. This apparatus includes a bushing which defines a bushing channel extending longitudinally axially therethrough and a bush aperture extending radially thereinto oriented approximately perpendicularly with respect to the bushing channel. A fluid housing is included extending into the bushing. This fluid housing defines a flashback chamber means therein which is adapted to receive fluid therewithin. A gripping mechanism is included extending around the bushing to facilitate manual operation of the hypodermic syringe apparatus. This construction defines a grip aperture extending therethrough which is positioned in relation with respect to the bushing aperture means preferably. A needle is included which defines a needle channel extending longitudinally therethrough. The needle is attached with respect to the fluid housing to facilitate fluid flow with respect thereto. For this purpose, the needle channel is in full fluid flow communication with respect to the flashback chamber defined within the fluid housing. A needle cover is included which is slideably movably positioned within the bushing channel and is movable from a retracted position within the bushing channel to a deployed position extending outwardly from the bushing channel toward and surrounding the needle for shielding thereof after use. A resilient biasing means such as a spring or the like is positioned within the bushing channel and is attached with respect to the needle cover for the purpose of continuously exerting a force thereagainst to continuously urge movement of the needle cover toward the deployed position thereof. A needle cover button is positioned extending through the grip aperture and through the bushing aperture into the bushing channel to selectively retain the needle cover in the retracted position responsive to being deactivated. The needle cover button will define a needle cover button hole extending therethrough which is selectively registrable with respect to the needle cover responsive to activation of the needle cover button to align the needle cover button hole with respect to the needle cover, and to facilitate passing thereof through the needle cover button hole to facilitate further movement of the needle cover to the deployed position thereof extending around and shielding the needle.

A locking mechanism is included for selectively preventing activation of the needle cover button to prevent movement of the needle cover to the deployed needle cover position when desired. This locking mechanism includes a first pin extending longitudinally within the bushing channel at a position adjacent to the needle cover button to prevent activating movement thereof. A second pin is also included extending longitudinally within the bushing channel at a position spatially disposed from the first pin. The second pin is positioned adjacent to the needle cover button to further facilitate activating movement thereof. A first unlocking button is positioned extending through the bushing at a position adjacent the first pin. The first unlocking button is responsive to being pressed to urge movement of the first pin toward the second pin. A second unlocking button is also included positioned extending through the bushing at a position adjacent to the second pin. The second unlocking button is responsive to being pressed to urge movement of the second pin toward the first pin. In this manner, the pressing of the first unlocking button and the second unlocking button, simultaneously, will cause the first and second pins to be positioned adjacent to one another and to align the first pin and the second pin with respect to the needle cover button slot thereadjacent in order to facilitate activation of the needle cover button to release the needle cover to allow movement thereof to the fully deployed position extending around the needle.

It is an object of the hypodermic syringe apparatus of the present invention to provide a needle guard assembly designed specifically for the purpose of shielding or protecting of a needle after use to prevent the spread of disease and/or infection thereby.

It is an object of the hypodermic syringe apparatus of the present invention to provide a construction for facilitating the safe disposal of single use hypodermic syringes in health environments.

It is an object of the hypodermic syringe apparatus of the present invention to provide a construction having a minimum number of movable parts to facilitate reliability and efficiency of operation thereof.

It is an object of the hypodermic syringe apparatus of the present invention to provide a coordinated three button sequentially operated construction for initially locking of the needle cover in place within the syringe and allowing movement of the needle cover toward the deployed position only after simultaneous pressing of a first and second unlocking button is performed simultaneously along with activation of a needle cover button.

It is an object of the hypodermic syringe apparatus of the present invention to provide a needle guard assembly which is generally tubular in configuration.

It is an object of the hypodermic syringe apparatus of the present invention to provide a needle guard assembly wherein a tubular needle guard extends outwardly to a deployed position completely surrounding the hypodermic needle.

It is an object of the hypodermic syringe apparatus of the present invention to provide a system for shielding a needle after use which is of minimal cost and is extremely easy to operate.

BRIEF DESCRIPTION OF THE DRAWINGS

While the invention is particularly pointed out and distinctly described herein, a preferred embodiment is set forth in the following detailed description which may be best understood when read in connection with the accompanying drawings, in which.

DETAILED DESCRIPTION OF THE PREFERRED EMBODIMENT

Figure 1A:
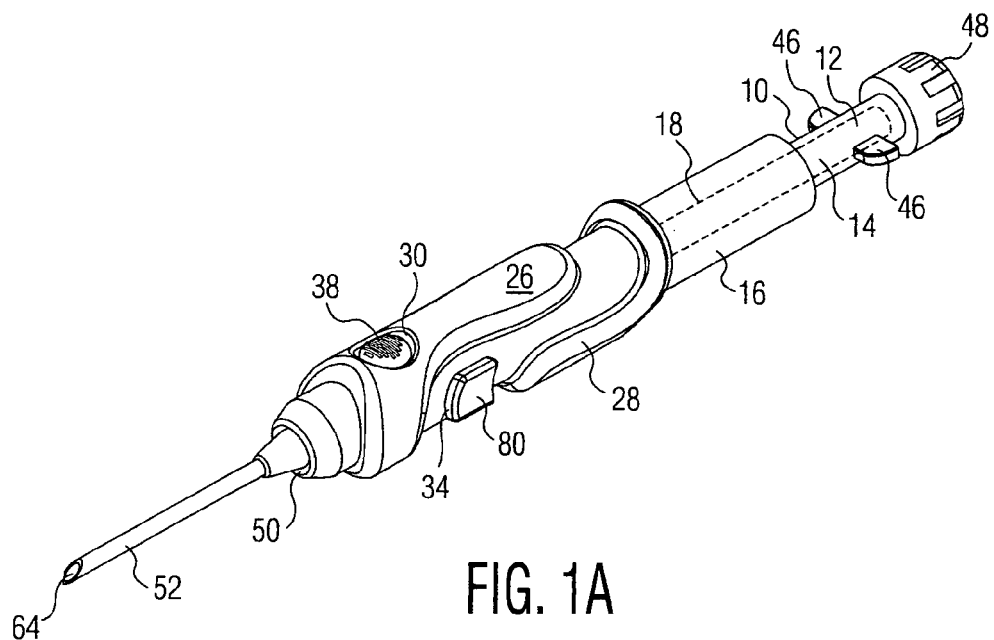
FIG. 1A is a perspective illustration of an embodiment of a hypodermic syringe apparatus of the present invention shown with the needle cover locked in the retracted position.
Figure 1B:
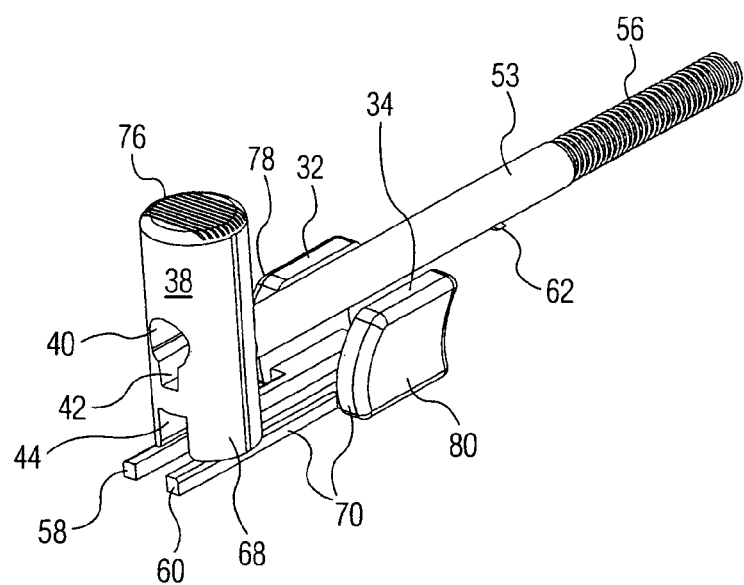
FIG. 1B is an illustration of the construction shown in FIG. 1A showing the internal parts including the needle cover button, the needle cover, the biasing means, and the first and second pins shown in the position locking the cover in the retracted position.
Figure 2A:
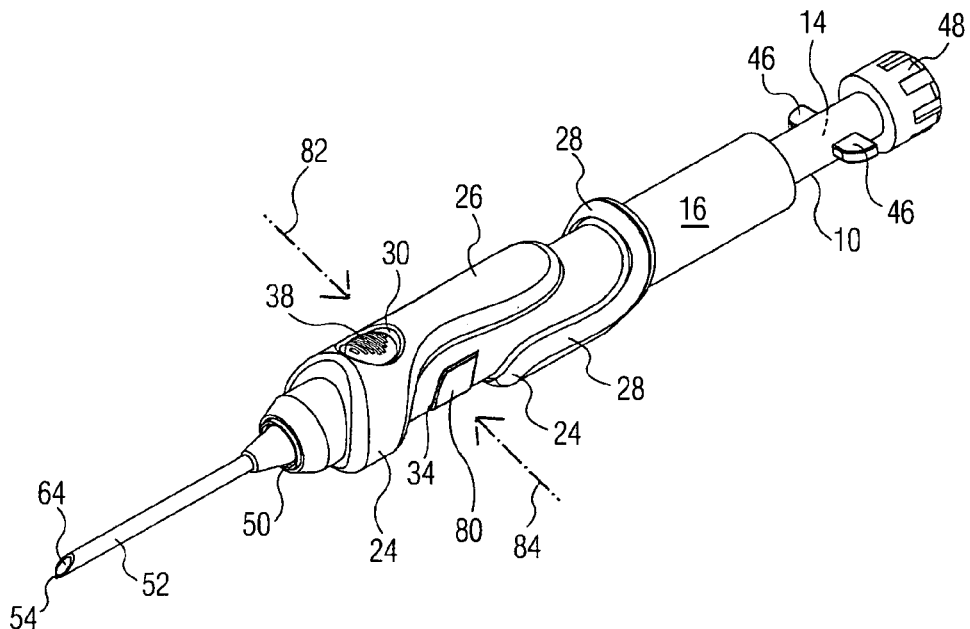
FIG. 2A is an illustration of the embodiment shown in FIG. 1A immediately after unlocking of the needle cover by simultaneously pressing of the first and second unlocking buttons.
Figure 2B:
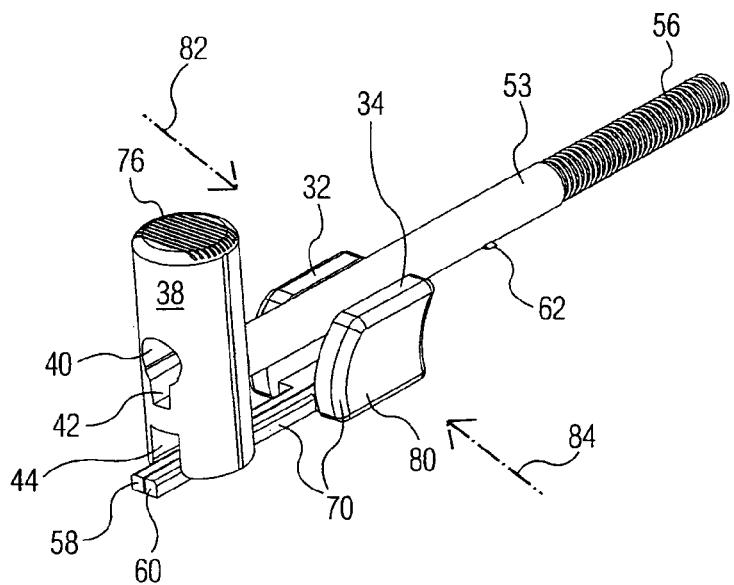
FIG. 2B is an illustration of the internal parts in position as shown in FIG. 2A immediately after pressing of the first and second unlocking buttons.

The present invention provides a hypodermic syringe apparatus having a needle guard assembly which makes subcutaneously injection shielding of the used needle a high priority. This construction includes a bushing 16 which comprises basically an enclosure which is usually of a tubular shape that houses the mechanism for covering the needle and other important working parts of the syringe of the present invention. The construction of the bushing 16 is such that it includes a bushing channel means 18 extending axially therethrough and a bushing aperture means 22 preferably oriented axially with respect to the bushing channel means 18 and most usually is oriented perpendicularly thereof. This bushing aperture means is designed to receive a needle cover button 38 therewithin. A fluid housing 10 is positioned immediately behind the bushing 16 preferably and defines a flashback chamber means 14 therewithin. Fluid housing 10 is designed to receive a fluid therewithin which fluid is in the process of either being injected through a needle 52 into a user, or is fluid which has been removed from the user through needle 52. With either purpose, the shielding of the used needle after use is achievable by the construction of the present invention. Preferably, the fluid housing 10 will be a tubular structure made with a transparent or translucent material which is connected to the bushing 16 and the needle 52 on one end, and has a common luer connection means 86 on the opposite end thereof. An end cap 48 is selectively engageable therewith to close the fluid housing 10 and seal the flashback chamber means 14 therewithin as desired.

The present invention further includes a gripping means 24 to facilitate manual manipulation and handling of the present apparatus. This gripping means 24 preferably includes a front gripping section 26 and a rear gripping section 28, which in this embodiment are shown spatially disposed from one another to facilitate grasping. The gripping means 24 is mounted upon the exterior portion of the bushing 16. Preferably the gripping means 24 will also define a grip aperture means 30 therein which is preferably in registration with the bushing aperture means 22 for the purpose of receiving a needle cover button 38 extending therethrough. The two parts of the gripping means 24 preferably will be molded to the bushing 16 for the purpose of guiding the fingers of a user to hold the syringe apparatus of the present invention in the proper position in a comfortable, safe and secure manner.

A first unlocking button 32 will be positioned extending through the right side of the bushing 16, and a second unlocking button 34 will be extending through the left side of the bushing 16. Each of these unlocking buttons are operative when pressed to unlock the needle cover 53 as an initial step toward releasing thereof such that it can move to a fully extended or deployed position completely surrounding the needle 52 for shielding thereof after usage.

The first unlocking button 32 will be positioned in engagement with a first pin 58 located on the right side of the interior of the bushing 16 within the bushing channel 18. A second pin 60 will be located within the bushing channel means 18 in the left portion thereof and will be positioned in abutment with respect to the second unlocking button 34. Pressing of the first unlocking button 32 and the second unlocking button 34 simultaneously will cause the first pin 58 and the second pin 60, which in the steady state position are separated from one another to move toward one another to become immediately adjacent with respect to each other as shown best in FIG. 3B. This movement comprises the first step toward achieving deployment of the needle cover 53 to the fully deployed needle position 88 extending around the needle 52. The needle 52 will preferably comprise a hollow tube of metal which is connected to the inside of the bushing 16 with one side extending completely to a position of engagement with respect to the flashback chamber means 14 and the opposite side normally comprising a sharp end which extends outside of the bushing 16 to facilitate initial placement thereof subcutaneously with respect to a patient for the purpose of either collecting or distributing subcutaneous fluid.

The bushing channel means 18 will define a needle cover void 50 therewithin. This embodiment comprises an annularly shaped space between the needle 52 and the bushing 16 within the bushing channel 18. In this manner, the needle cover 53, particularly when in the configuration shown in this embodiment wherein it has the shape of a hollow tube, can slide along this void or track inside the bushing channel means 18 of the bushing 16 to the fully deployed needle cover position 88 shown best in FIGS. 6A and 6B.

A locking means 70 is configured within the construction of the hypodermic syringe apparatus of the present invention comprising multiple parts, in particular, including the first unlocking button 32, the second unlocking button 34, the first pin 58, the second pin 60, and the entire construction of the needle cover button 38.

Needle cover button 38 preferably includes a needle cover button hole 40 extending axially completely therethrough generally of a round shape with a needle cover button channel 42 in communication therewith and extending downwardly from the needle cover button hole 40. Furthermore, the needle cover button 38 will define in the lowermost surface thereof a needle cover button slot 44 which is selectively movable vertically with the needle cover button 38. Needle cover button 38 preferably extends through the grip aperture means 30 of the front gripping section 26 and extends further into the bushing aperture means 22 defined in the bushing 16 to a position such that it extends across the bushing channel 18 and selectively blocks movement of the needle 52 along the bushing channel means 18 prior to activation of the needle cover button 38. Preferably the needle cover button 38 is movable between a de-activated position 68 and an activated position 66.

Prior to activation the body of the needle cover button 38 prevents movement of the needle cover 53 toward the fully deployed needle cover position 88. However once activated, the needle cover button 38 will be pressed axially inwardly to achieve alignment of the needle cover button hole 40 with respect to the needle cover 53. Once this alignment is achieved, then the needle cover 53 is free to move through the needle button hole 40 of needle cover button 38. This movement is achieved due to the forcible bias exerted thereagainst by the resilient biasing means 56 which in this embodiment takes the form of an actuator spring means. This spring 56 urges the needle cover 53 to move along the needle cover void 50 until it reaches the fully deployed needle cover position 88 wherein the generally tubular needle cover 53 will completely surround and protect the needle 52 and prevent unwanted sticking therefrom after the desired use. It is important that the needle cover 53 be maintained in the fully deployed needle cover position 88, and be incapable of any return movement toward the retracted position and this is achieved by the inclusion of a needle cover tab means 62 which will spring laterally outwardly from the needle cover 53. Once it reaches the fully deployed needle cover position 88, the lateral protrusion of the needle cover tab means 62 will prevent the needle cover 53 from moving away from the deployed needle cover position 88 once it has reached this position since return movement through the needle cover button hole 40 will be blocked by this laterally and outwardly extending tab means 62.

The needle 52 is shaped like a conventional needle in that it is generally tubular and will define internally therein a needle channel means 64 extending therealong to facilitate fluid flow once the needle has penetrated to a subcutaneous level relative to the user.

Manipulation of the hypodermic syringe apparatus of the present invention is significantly enhanced by the inclusion of grip wings 46 and end cap 48. The end cap 48 further provides a means for sealing the end of the fluid housing 10 to seal the flashback chamber 14. However, it should be appreciated that removal of the end cap 48 is often needed in order to transfer fluids from the internal portion of the flashback chamber means 14 to another location for medical purposes especially when used in the mode wherein fluid is withdrawn from the subcutaneous area of a patient by the hypodermic syringe apparatus of the present invention. Full surrounding engagement of the needle cover 53 is achieved with respect to the needle 52 because the needle cover 53 is generally tubular in shape and thus defines a containment chamber means 72 therewithin, adapted to receive and completely surround and protect the needle 52 when the needle cover 53 is in the fully deployed needle cover position 88. The front portion of the needle 52 will include a front containment opening 74 which is in full fluid flow communication with the containment chamber means 72 which allows the needle cover 53 to move to the fully deployed needle cover position 88 extending around and completely shielding the needle 52 therewithin.

The activation of the needle cover button 38 of the present invention is an important aspect of the present invention, and for this reason a plurality of serrations 76 are preferably defined in the external exposed portion thereof to facilitate engagement between the fingers of a user and the needle cover button 38. It should also be appreciated that the movement of the first unlocking button 32 and the second unlocking button 34 toward one another by simultaneous pressing thereof is made along pressing direction arrows 82 and 84. Arrow 82 shows the direction of pressing for the first unlocking button 32, and pressing direction arrow 84 shows the direction for pressing of the second unlocking button 34. To further facilitate this simultaneous pressing movement, the first unlocking button 32 will preferably define a first arcuate surface 78 thereon which is preferably concave. Similarly, the second unlocking button 34 will preferably define a second arcuate surface 80 thereon which is preferably concave to facilitate engagement with the finger of a user. In this manner, simultaneous movement of the first and second unlocking buttons 32 and 34 along pressing direction arrows 82 and 84 will be able to be performed simultaneously to achieve unlocking of the apparatus of the present invention. Thereafter, the serrations 76 will enhance engagement between the fingers of a user and the uppermost portion of the needle cover button 38 such that the needle cover button 38 can be fully activated and in this manner release the needle cover 53 such that it can move along the needle cover void 50 to the fully deployed needle cover position 88 extending completely around and protecting and guarding of the needle 52.

Use of the hypodermic syringe apparatus of the present invention is shown in various drawings enclosed herein. The inserting and removing of a needle 52 will be achieved by a person while holding the bushing 16 which is generally tubular in shape near the first and second unlocking buttons 32 and 34 located on the right and left portions, respectively, of bushing 16. Normally, the person will use a thumb and index or middle finger in engagement with each of the first arcuate surface 78 of button 32 and the second arcuate surface 80 of button 34. In this manner, simultaneous pressing thereof will achieve. These surfaces along with the configuration of the configuration of the front and rear gripping sections 26 and 28 of gripping means 24 are shaped and formed in such a particular way that the fingers of the user will easily and comfortably be positionable to achieve a secure grip. The use of the two gripping sections 26 and 28 for the gripping means 24 will enhance the ability of the fingers to be in the safest position possible in order to create a sturdy grip to significantly reduce any possible slipping. The grip 24 is also unique because it guides the user into holding the hypodermic syringe apparatus of the present invention in a natural manner, and is can be used easily by a person who is naturally left handed or right handed. The hypodermic syringe apparatus of the present invention facilitates the operation of this construction with a single hand, rather than requiring a two handed operation which can significantly be more cumbersome. Further, the configuration of the gripping means 24 will elevate the hypodermic syringe apparatus above the skin of a user in certain areas and give full breathability to the skin by letting air travel under the exterior of the needle 52. Even when the hypodermic syringe is taped to the body of a user for long periods, such as with intravenous connections, the configuration of the grip 24 into two separate parts, namely, the front gripping section 26 and the rear gripping section 28, will slide onto the bushing 16 or can be molded into the configuration of the bushing 16, and, in that manner, create a single integral easily gripped construction for the bushing 16.

When the user is injecting the needle 52 subcutaneously with respect to a patient, it is important that none of the three activating buttons be pressed or activated. That is, it is important that the needle cover button 38 and the first unlocking button 32 and the second unlocking button 34, are not pressed or activated in any manner during injection during subcutaneous injection of needle 52. In this manner, the needle cover 53 will be maintained in the steady state initial retracted needle cover position within the bushing 16. A successful injection will result in fluid ultimately filling the flashback chamber means 14 which is of a size and shape to conveniently engage any conventional luer lock fitting of external equipment for any purpose.

Preferably, the resilient spring biasing means 56 will be approximately the same diameter as the needle cover 53 such that it will press the needle cover 53 against the solid portion against the solid body portion of the needle cover button 38 and thus allow the needle cover 53 to be held in position within the bushing 16 where it is retracted both before and during subcutaneous penetration by the needle 52. The unlocking button hinge, namely the first pin 58 and the second pin 60, are connected to the unlocking buttons 32 and 34, and block the needle cover button 38 from being activated and moving downwardly as shown in FIG. 1A.

Thus, before activation the force exerted by the resilient biasing means 56 will not be able to move the needle cover 53 away from the retracted position. Prior to activation, the unlocking buttons 32 and 34 will be protruding slightly from the exterior surface of the bushing 16, and the unlocking button pins 58 and 60 will be spatially disposed from one another. In this position, the needle cover button 38 will be in the outwardly most extended position which is the deactivated position. Also in this position, the needle cover 53 will be positioned within the bushing channel 18 of bushing 16 between the needle cover button 38 and the resilient biasing actuator spring 56. In this position, the spring will be compressed between the bushing 16 and the needle cover 53.

However, after the needle 52 is removed from the patient, the needle cover 53 preferably will become activated by sequential and/or simultaneous operations of one or more of the three buttons. To achieve activation, the right and left unlock buttons 32 and 34 are pressed inwardly along direction lines 82 and 84 toward one another preferably by being pressed together or squeezed between the thumb and middle finger of a user. This movement causes the right and left or first and second unlocking buttons 32 and 34 to move horizontally toward one another, which then moves the left and right unlocking button pins 58 and 60 toward one another to a final position wherein they are immediately adjacent to one another. Thereafter, the needle cover button 38 is activated by pressing down by the index finger of the user.

Figure 3A:
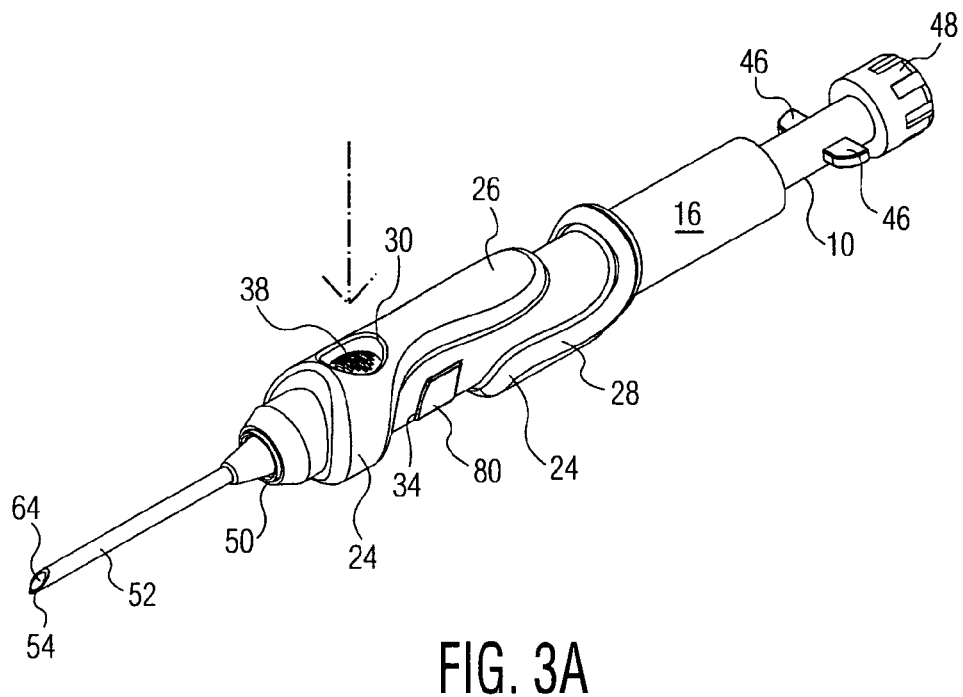
FIG. 3A is a perspective illustration of the embodiment shown in FIG. 2A immediately after activation of the needle cover button.
Figure 3B:
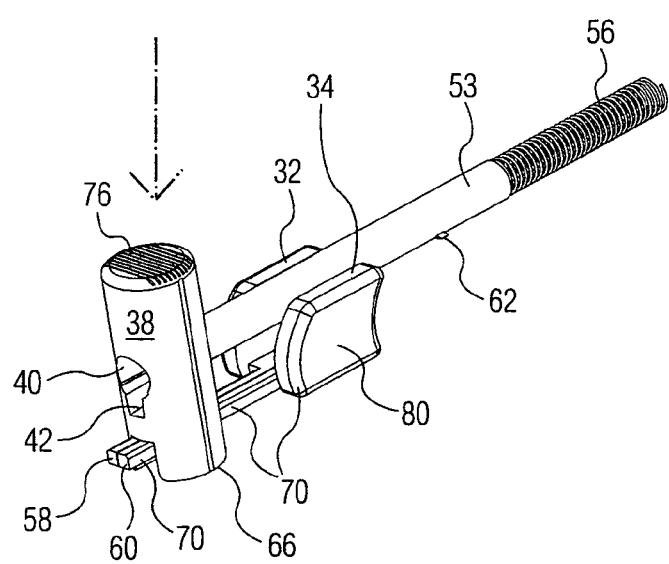
FIG. 3B is an illustration of the internal working parts of FIG. 3A immediately after activation of the needle cover button.
Figure 4A:
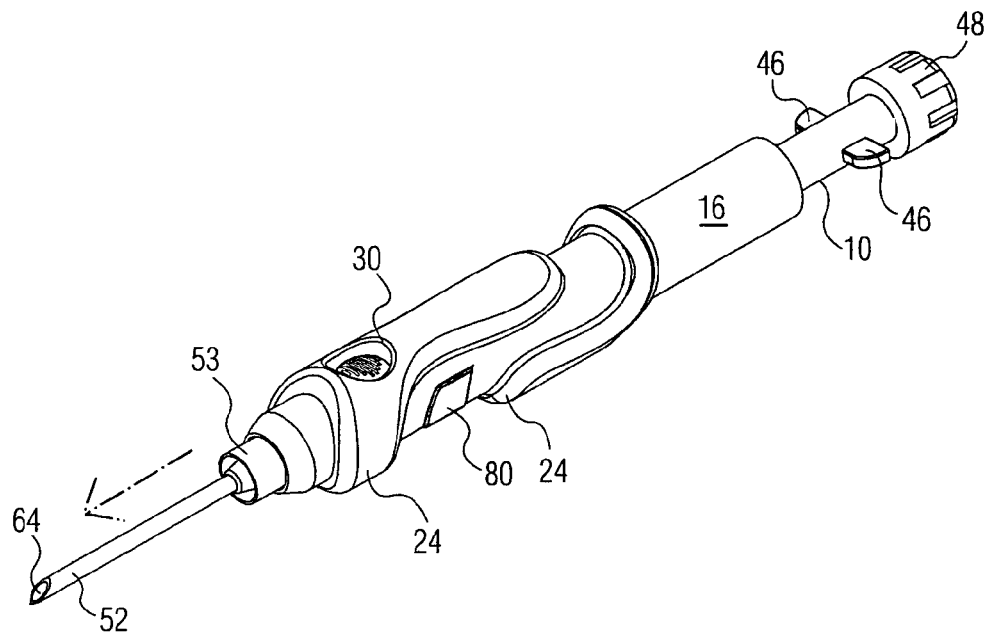
FIG. 4A is a perspective illustration of the embodiment shown in FIG. 3A shortly after the position shown in FIG. 3A wherein the needle cover is initiating deployment by moving to the left as shown in FIG. 4A toward but having not yet reached the fully deployed position.
Figure 4B:
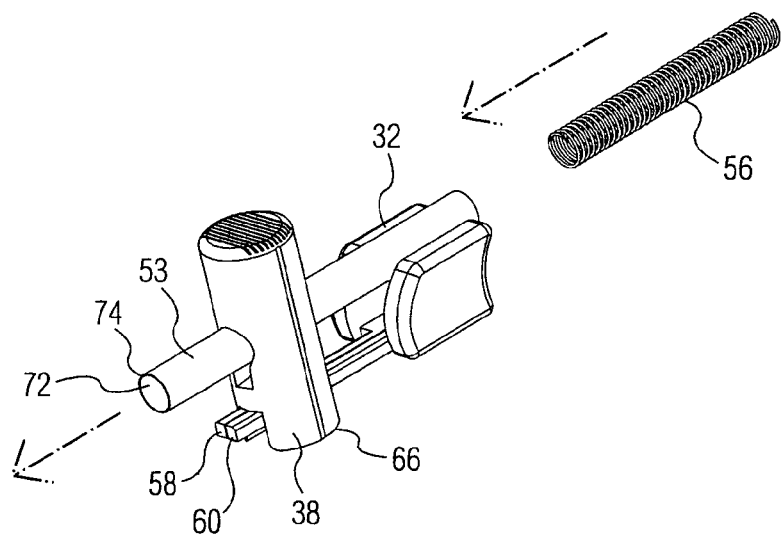
FIG. 4B is an illustration of the internal parts within the embodiment shown in FIG. 4A in the same position as shown in FIG. 4A.
Figure 5A:
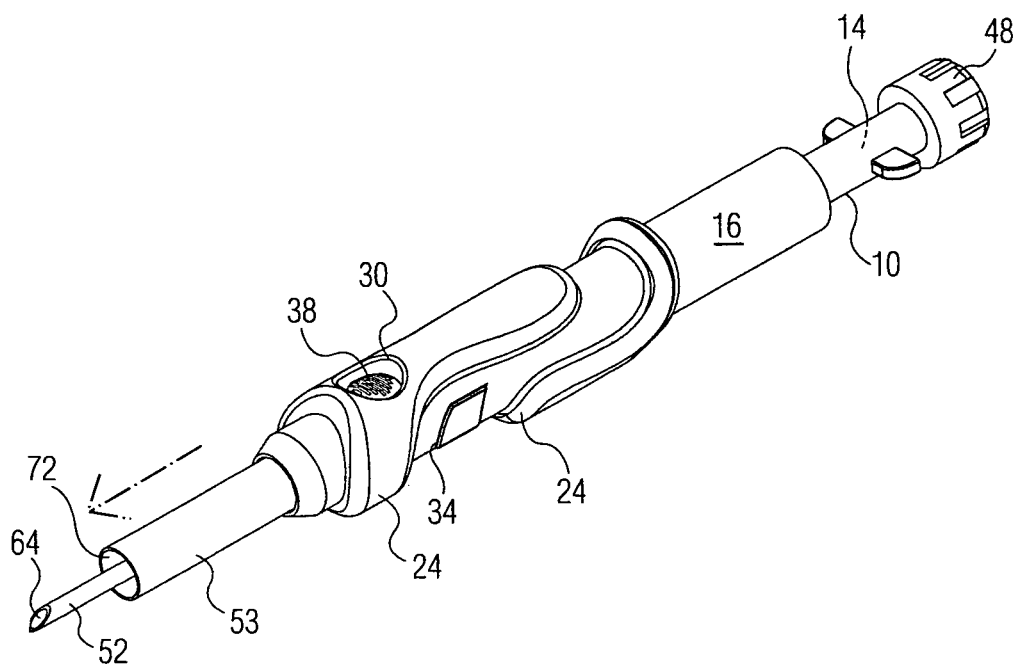
FIG. 5A is a perspective illustration of the embodiment as shown in FIG. 4A with the needle cover further extended toward the fully deployed position but not yet having reached the fully deployed position.
Figure 5B:
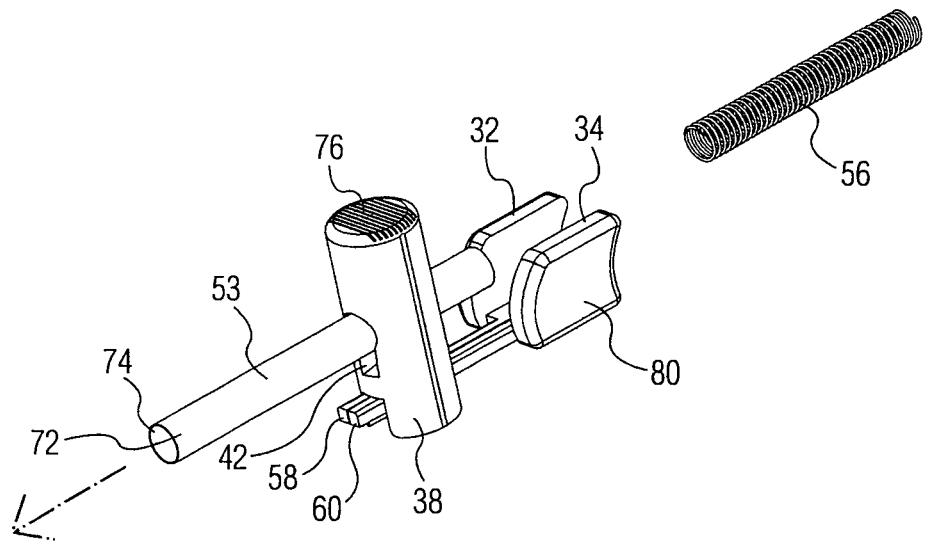
FIG. 5B is an illustration of the internal parts within the hypodermic syringe shown in FIG. 5A shown at the same position as shown in FIG. 5A.

As the needle cover button 38 moves downwardly as shown in FIGS. 3A and 3B. The needle cover button slot 44 will slide downwardly to a position extending over and around the first and second unlocking buttons 32 and 34 while the needle cover button channel 42 allows the needle cover button 38 to move without contacting the needle 52. Simultaneously, the needle cover 53 will become registered or line up with the needle cover button hole 40. This alignment allows the needle cover 53 to slide into the needle cover button hole 40 in a direction toward the needle 52. Thus, the needle cover 53 will move along the needle cover void 50 which is an annular space between the needle 52 and the bushing 16. Due to the force exerted thereon by the resilient actuator spring 56 such that it can move to a position completely covering and shielding the needle 52, which is defined as the fully deployed needle cover position 88 as shown best in FIGS. 6A and 6B. In this manner, any excess fluids can be collected from the needle area and unwanted piercing by the needle 52 after subcutaneous use thereof will be prevented. Preferably, the length of the needle cover 53 is greater than the length of the needle 52, and it is preferably that the needle cover 53 will stop before completely exiting the bushing 16, but after it is fully covered and surrounded by the needle 52. This is a single use action, and once the needle cover 53 is deployed, the hypodermic syringe apparatus of the present invention should be discarded. It is the small needle cover tab 62 that prevents the needle cover 53 from moving backwardly or from the fully deployed needle position to a retracted position. The needle cover button 38 stops the needle cover 53 from moving backward by contacting the needle cover tab and creating the needle cover tab 62, and in this manner creating a lock that cannot be disabled. This construction prevents accidental needle stick injuries because the needle is prevented from being exposed again and thus the hypodermic syringe apparatus can be easily and safely discarded.

Figure 6A:
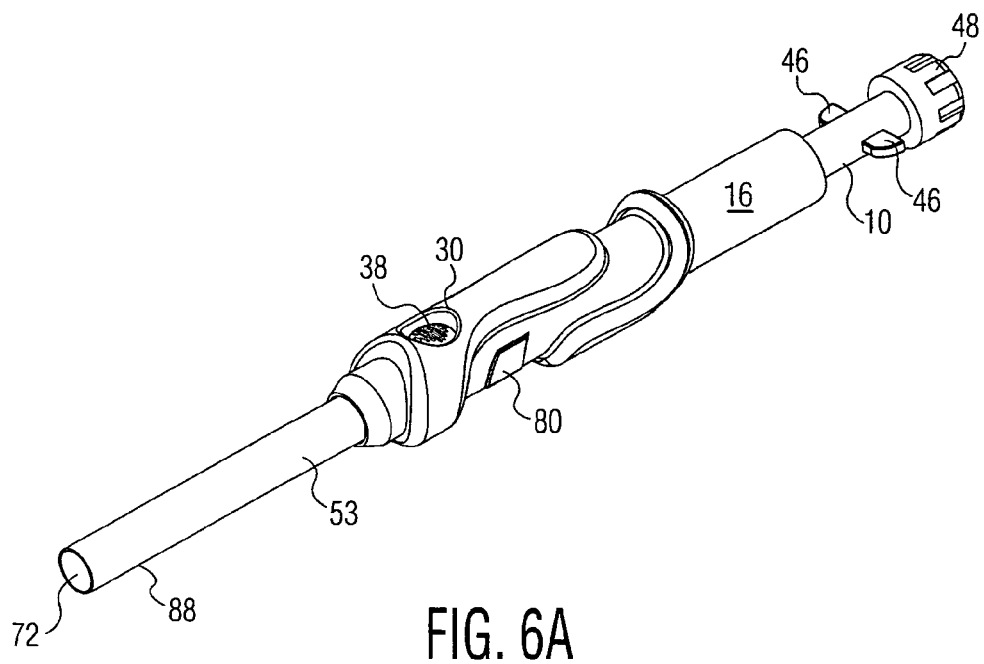
FIG. 6A is a perspective illustration of an embodiment of the hypodermic syringe of the present invention as shown in FIG. 5A wherein the needle cover has moved further to be located in the fully deployed position.
Figure 6B:
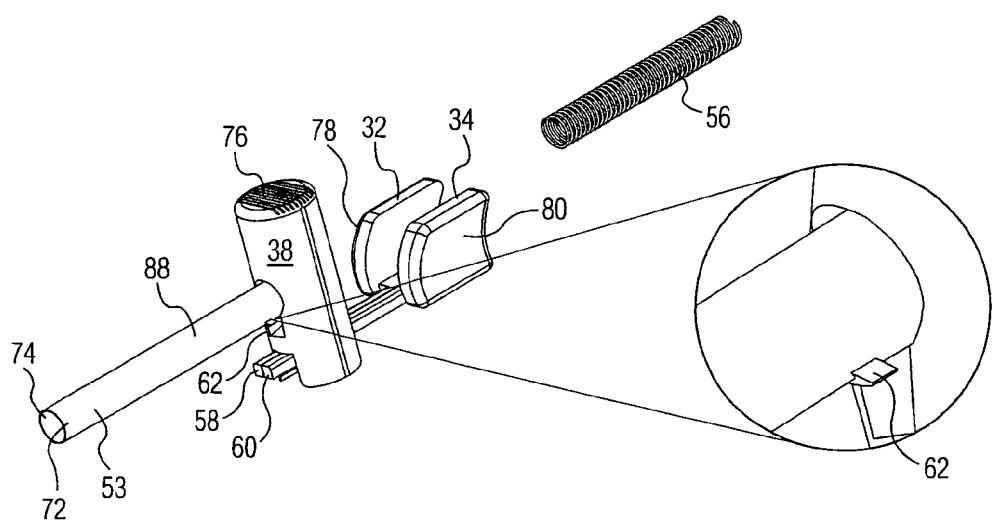
FIG. 6B is an illustration of the internal parts of the embodiment shown in Figure A shown in the same position as is the apparatus of Figure A.
Figure 7:
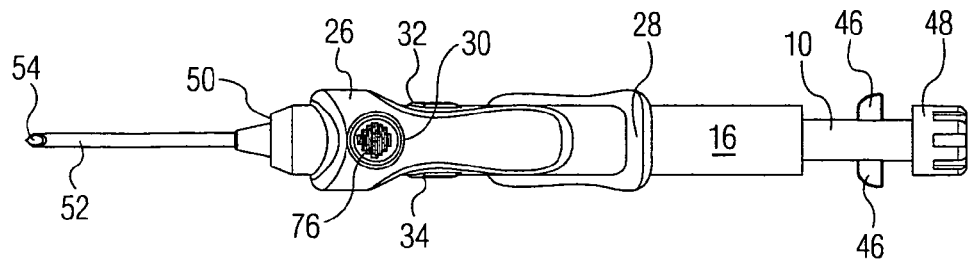
FIG. 7 is a top plan view of an embodiment of the hypodermic syringe apparatus of the present invention.
Figure 8:
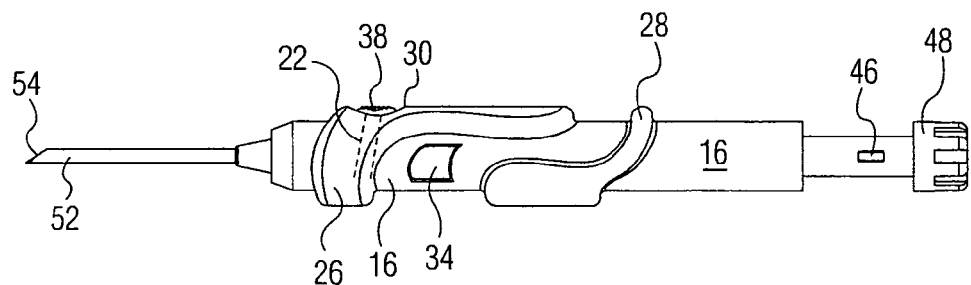
FIG. 8 is a left side plan view of the embodiment shown in FIG. 7.
Figure 9:
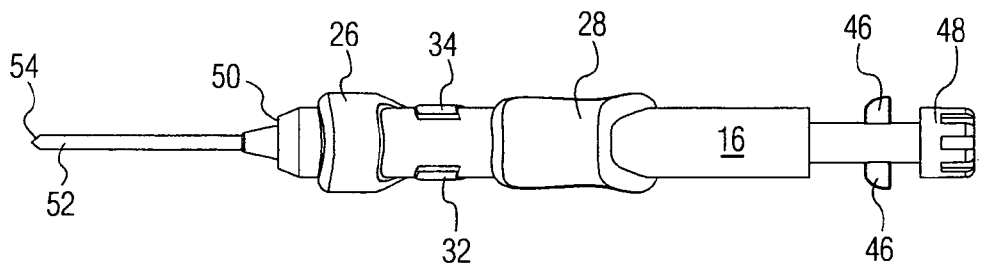
FIG. 9 is a bottom plan view of the embodiment shown in FIG. 7.
Figure 10:
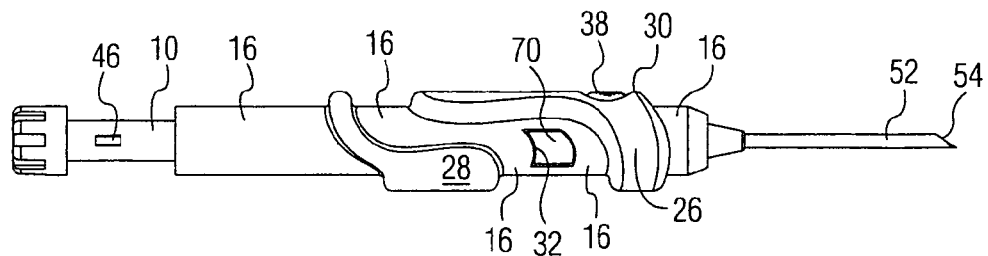
FIG. 10 is a right side plan view of the embodiment shown in FIG. 7.
Figure 11:
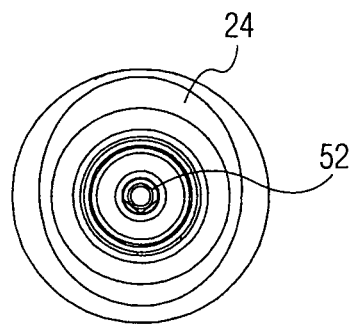
FIG. 11 is an end plan view of the embodiment shown in FIG. 7 of the hypodermic syringe apparatus of the present invention shown taken from the right.
Figure 12:
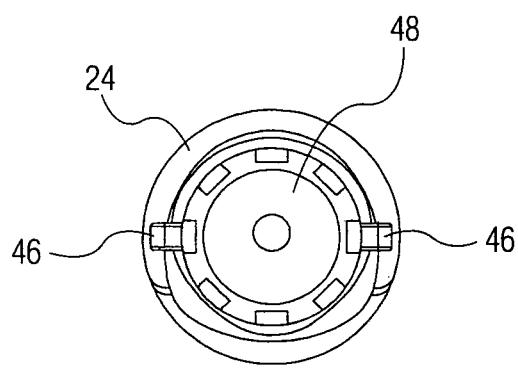
FIG. 12 is a rear plan view of the embodiment shown in FIG. 7 as taken from the left.
Figure 13:
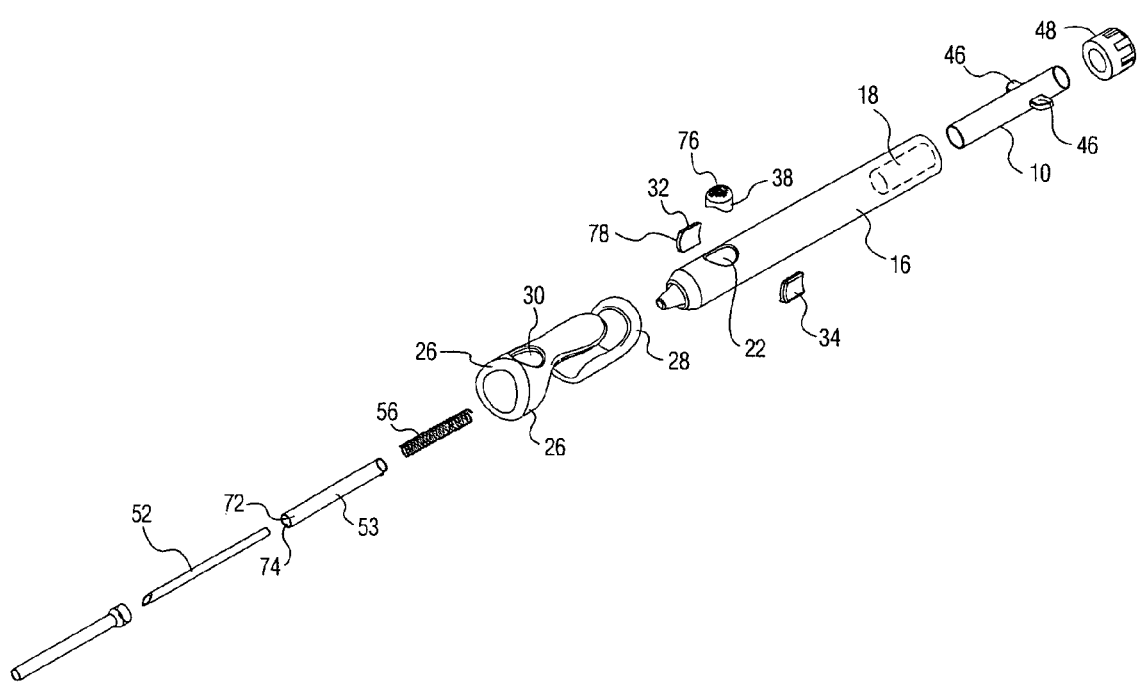
FIG. 13 is an exploded view of an embodiment of the hypodermic syringe apparatus of the present invention.

After activation, the hypodermic syringe apparatus of the present invention is extended and locked into position best shown in FIGS. 6A and 6B which shows the needle cover 53 located in the fully deployed needle cover position 88. To allow this movement, the user must press inwardly on the first unlocking button 32 on the right, and the second unlocking button 34 on the left. Such pressure exerted by preferably the thumb and forefinger of the user will cause the unlocking buttons 32 and 34 to move toward one another. This mutual movement of buttons 32 and 34 will cause the first pin 58 on the right and the second pin 60 on the left to be moved toward one another to a position where they will be immediately adjacent one another. In this position, when the needle cover button 38 is activated or pressed downwardly, the needle cover button hole 40 defined within needle cover button 38, will come into registration with the needle cover 53. This coaxial alignment between the needle cover 53 and the needle cover button hole 40 in the needle cover button 38 will allow the needle cover 53 to easily pass therethrough responsive to the pressure exerted thereon by the resiliently biasing actuator spring means 56.

Figure 14:
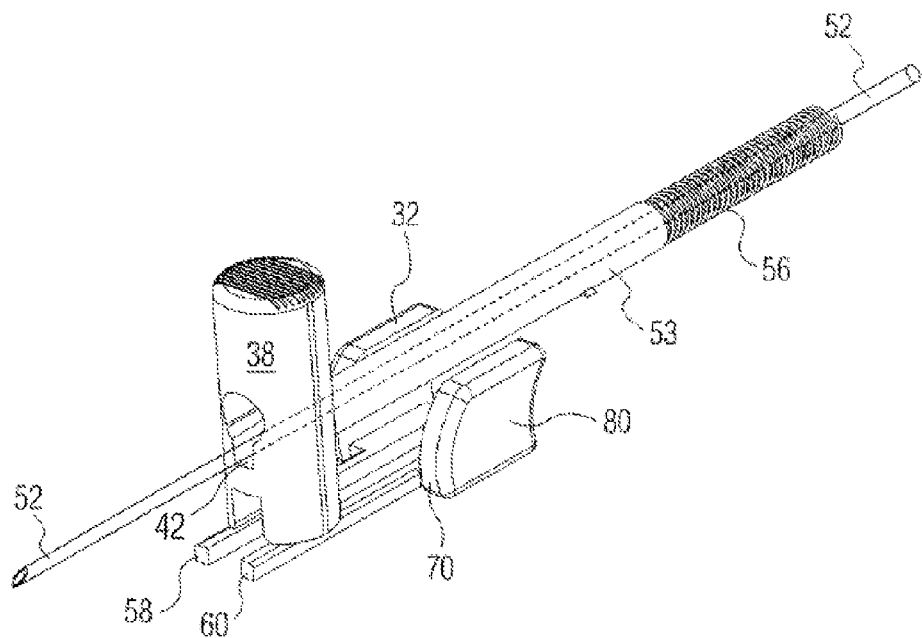
FIG. 14 is a view of the internal parts of the present invention shown in the same position as FIG. 1B, but illustrating the positioning of the needle therewithin with the needle initially retained extending through the needle cover button slot.
Figure 15:
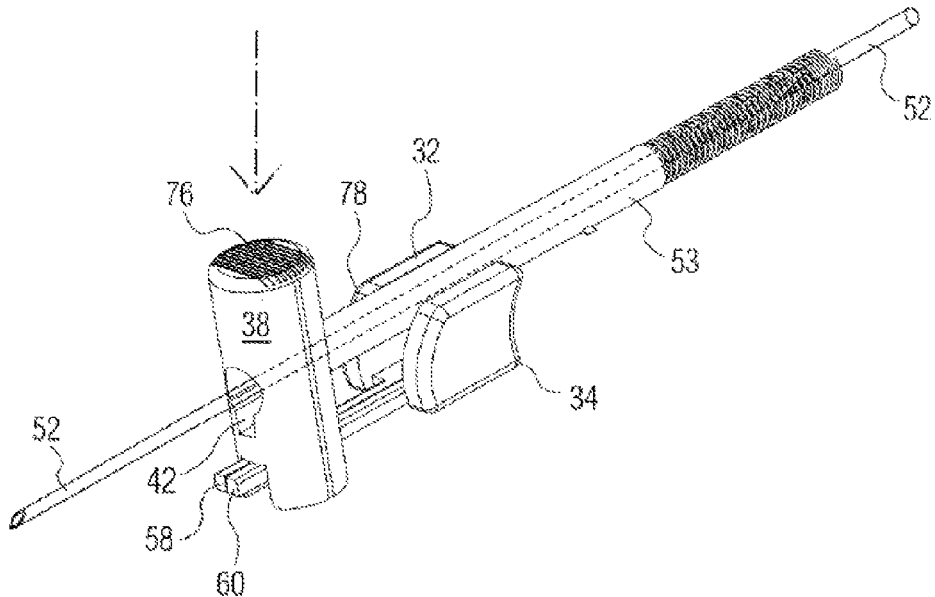
FIG. 15 is an illustration of internal parts of an embodiment of the present invention shown in the position illustrated in FIG. 3B, however showing the positioning of the needle after activation of the needle cover button wherein the needle is located extending through the needle cover button hole.

The movement described immediately hereabove is also shown in the FIGS. 14 and 15. FIG. 14 shows the hypodermic syringe apparatus of the present application before activation. In this position, the needle cover button channel 42 cradles the needle 52. The central and rear portion of the needle 52 are both covered at this time by the needle cover 53, and compressed resilient biasing means 56. The body of the needle cover button at this position prior to activation will effectively block the needle cover 53 from entering the needle cover button hole 40 because they are not aligned with respect to one another.

Figure 16:
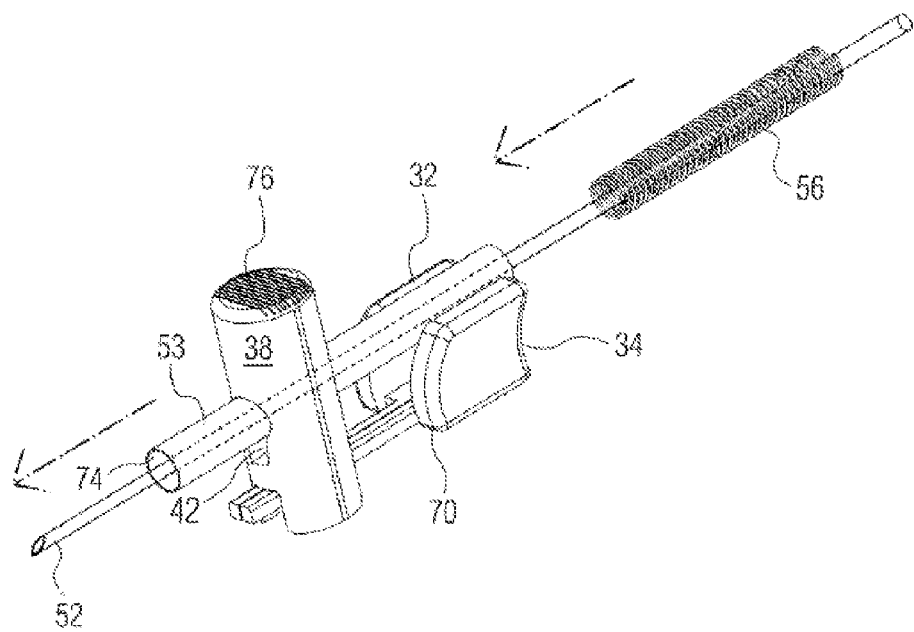
FIG. 16 is an illustration of a preferred embodiment of the present invention in the position shown in Figure B and here showing the needle extending through the needle cover button hole with the needle cover partially in transit moving toward the deployed position.
Figure 17:
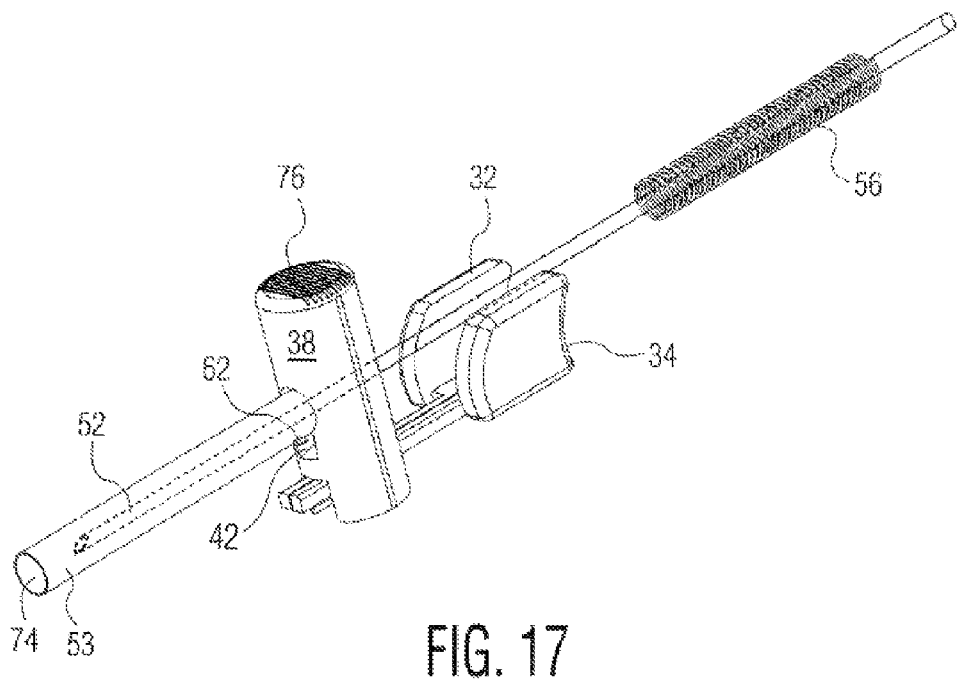
FIG. 17 is an illustration of an embodiment of the internal parts of the present invention shown in the position set forth in FIG. 6B wherein the needle cover is in the fully deployed position.

Moving up from FIG. 14 to FIG. 15, it is apparent that FIG. 15 shows the apparatus of the present invention after removal of the needle 52 from the patient. At this point, the healthcare worker will press the first unlocking button 32 and the second unlocking button 34 toward one another which will urge the first pin 58 and second pin 60 to also move toward one another to a position where they are virtually adjacent. Thereafter, the healthcare worker will activate the needle covering option of this design by activating the needle cover button 38 by pressing downwardly thereon normally with the forefinger, while in engagement with respect to the serrations 76 defined in the uppermost portion thereof. Responsive to this activation, the needle cover button 38 will move downwardly and the needle 52 will now be positioned in the needle cover button hole 40 rather than in the needle cover button channel 42. Because initially needle 52 will remain stationary immediately after activation prior to the needle cover button hole 40 moving downwardly sufficiently to come into alignment with the needle cover 53. Once the needle cover button 38 is moved sufficiently downwardly that the needle cover button hole 40 comes into registration with the needle cover 53, it will allow the needle cover 53 to move through the needle cover button hole 40 and initiate its movement toward the fully deployed needle cover position 88. FIG. 16 shows the apparatus of the present invention at an intermediate stage during movement thereof toward the fully deployed needle cover position 88. The needle cover button hole 40 has lined up with the needle cover 53 and the needle cover 53 is passed partially therethrough and is moving toward the fully deployed needle cover position 88. The spring or other resilient biasing means 56 urges the needle cover 53 to initiate this movement. FIG. 17 shows the final position of the needle cover 53 after movement such that it completely surrounds and protects the needle 52. Preferably the front containment opening 74 defined in the front of the generally tubular needle 52 will extend beyond the needle tip and in this manner assure effective shielding thereof. In this position, note that the needle covered tab 62 has deployed thus preventing any backwards movement of the needle cover 53 away from the deployed position, and thus it is locked in the fully deployed needle cover position 88.

Figure 18A:
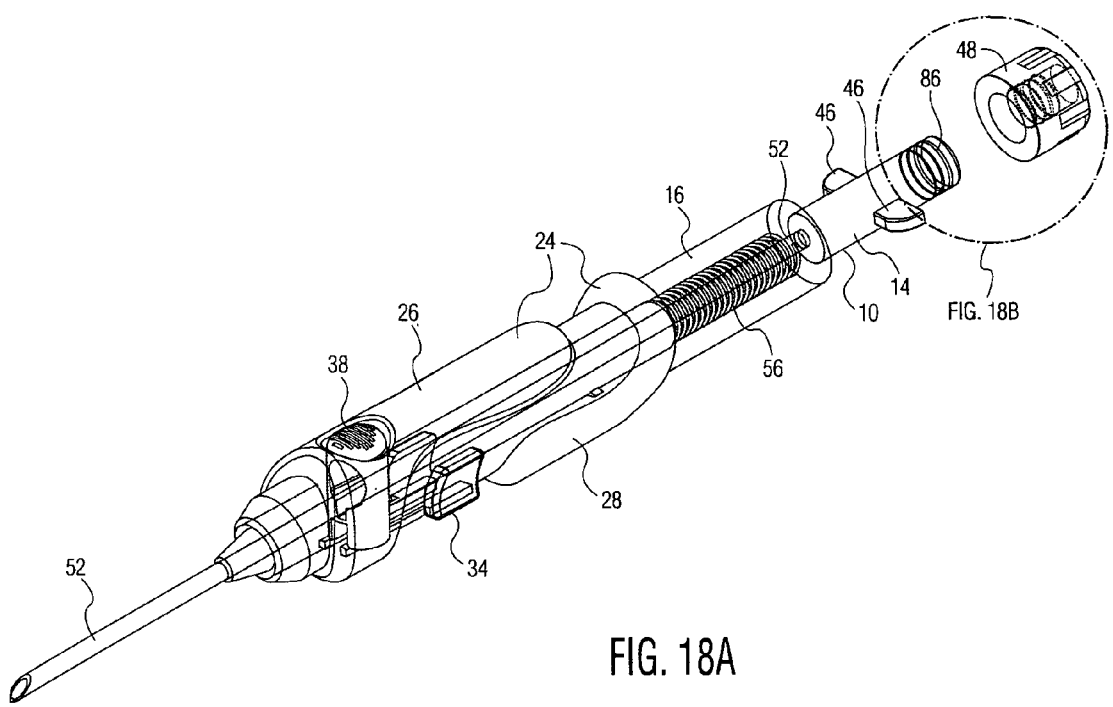
FIG. 18A is an illustration of an embodiment of the present invention which more clearly shows the fluid flow communication between the needle and the flashback chamber means.
Figure 18B:
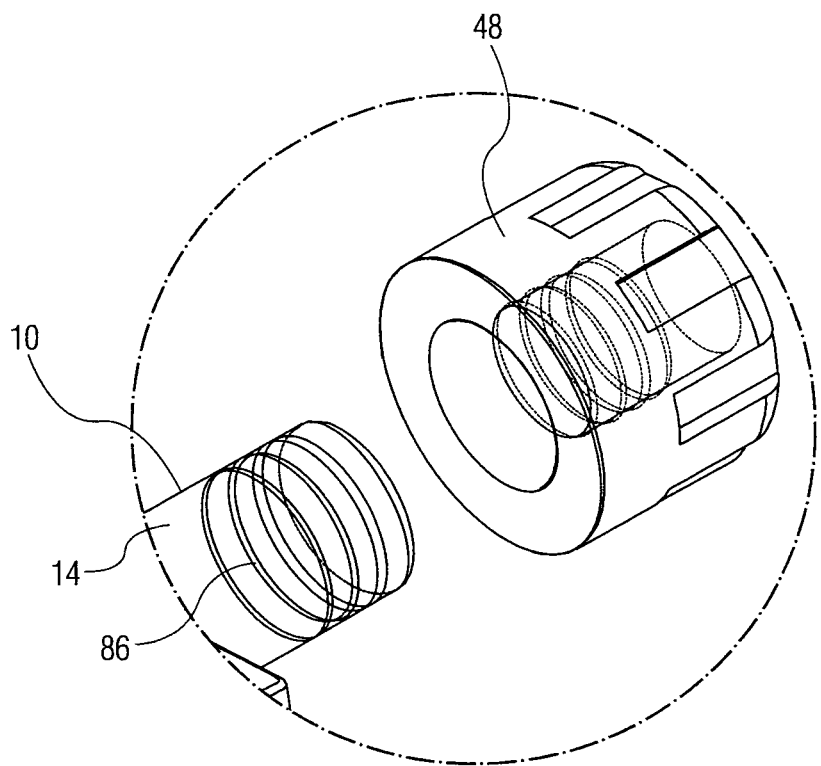
FIG. 18B is an exploded view thereof showing the interconnection between the end cap and the end of the fluid housing and flashback chamber means therewithin.

FIG. 18A and FIG. 18B include an exploded view of the fluid flow communication between the internal needle channel means 64 of needle 52, and the flashback chamber means 14 defined within the fluid housing 10. Fluid housing 10 provides the means for connecting fluid flow if desired with respect to any external medical equipment. For example, in this embodiment, a female luer lock connection 86 is shown at the outer end of the flashback chamber means 14 of the fluid housing 10, to facilitate connecting of the end of the syringe apparatus of the present invention with respect to any external equipment as may be needed for any purpose. Such a connection would of course require the removal of the end cap 48 from engagement with respect to this luer lock connection 86.

While particular embodiments of this invention have been shown in the drawings and described above, it will be apparent that many changes may be made in the form, arrangement and positioning of the various elements of the combination. In consideration thereof, it should be understood that preferred embodiments of this invention disclosed herein are intended to be illustrative only and not intended to limit the scope of the invention.

I claim:

1. A hypodermic syringe apparatus comprising:
   a bushing defining a bushing channel extending longitudinally axially therethrough and a bushing aperture extending radially thereinto oriented approximately perpendicularly with respect to said bushing channel;
   a fluid housing extending into said bushing, said fluid housing defining a chamber adapted to receive fluid therewithin;
   a needle defining a needle channel extending longitudinally therethrough, said needle being attached with respect to said fluid housing and in fluid flow communication with respect to the chamber;
   a needle cover slideably movably positioned within said bushing channel and being movable from a retracted position within said bushing channel to a deployed position extending outwardly from said bushing channel toward and surrounding said needle;
   a resilient biasing means positioned within said bushing channel and configured to bias said needle cover toward the deployed position thereof;
   a needle cover button, having a body extending along an axis between first and second ends, positioned through said bushing aperture such that said first end is accessible through said bushing aperture and said second end extends into said bushing channel, said needle cover button defining a needle cover button hole extending therethrough perpendicular to said axis thereof, the needle cover button hole is selectively registrable with respect to said needle cover responsive to activation of said needle cover button to align said needle cover button hole with respect to said needle cover and to facilitate passing thereof through said needle cover button hole to facilitate movement of said needle cover to the deployed position, said needle cover button further defining a needle cover button slot extending through said second end with the second end defining contact surfaces on opposed sides of said needle cover button slot;
   a locking means to selectively prevent activation of said needle cover button, said locking means comprising:
      a first pin having a major axis extending between first and second ends thereof, said first pin extending longitudinally within said bushing channel at a position adjacent to one of said needle cover button body second end contact surfaces and with said first pin major axis perpendicular to said body axis;
      a second pin having a major axis extending between first and second ends thereof, said second pin extending longitudinally within said bushing channel at a position spatially disposed from said first pin, said second pin being positioned adjacent to said other of said needle cover button body second end contact surfaces and with said second pin major axis perpendicular to said body axis;

a first unlocking button positioned extending through said bushing at a position adjacent said first pin, said first unlocking button configured to urge movement of said first pin toward said second pin;

a second unlocking button positioned extending through said bushing at a position adjacent said second pin, said second unlocking button configured to urge movement of said second pin toward said first pin, wherein pressing of said first unlocking button and said second unlocking button simultaneously causes said first pin and said second pin to be positioned adjacent to one another and to align said first pin and said second pin with respect to said needle cover button slot to facilitate activation of said needle cover button wherein said first and second pins are received in said needle cover button slot and said needle cover button moves to a position wherein said needle cover button hole is registered with said needle cover to release said needle cover to allow movement thereof to the deployed position extending around said needle.

2. A hypodermic syringe apparatus according to claim 1 wherein said bushing is generally cylindrical in shape and wherein said bushing aperture extends radially though said bushing oriented perpendicularly with respect to said bushing channel extending longitudinally axially therethrough.

3. A hypodermic syringe apparatus according to claim 1 wherein pressing of said first unlocking button and said second unlocking button simultaneously will facilitate activating movement of said needle cover button by moving said needle cover button toward said first and second pin and allowing said first and second pin to be become positioned within said needle cover button slot responsive to said needle cover button moving to the activated position.

4. A hypodermic syringe apparatus according to claim 1 wherein said resilient biasing means comprises an actuator coil spring.

5. A hypodermic syringe apparatus according to claim 1 wherein said needle cover is tubularly shaped and defines a containment chamber therein and a front containment opening therein in full fluid flow communication with respect to said containment chamber.

6. A hypodermic syringe apparatus according to claim 5 wherein positioning of said needle cover in the deployed position will place the needle cover in a position completely surrounding said needle with said needle positioned entirely within said containment chamber.

7. A hypodermic syringe apparatus according to claim 1 wherein said first unlocking button and said second unlocking button are positioned diametrically oppositely with respect to one another within said bushing.

8. A hypodermic syringe apparatus according to claim 1 wherein said needle cover button defines serrations in the first end thereof in order to facilitate manual activation thereof.

9. A hypodermic syringe apparatus according to claim 1 wherein said first unlocking button includes a first arcuate surface thereon and said second unlocking button includes a second arcuate surface thereon to facilitate simultaneous pressing thereof manually toward one another.

10. A hypodermic syringe apparatus according to claim 1 wherein said first pin and said second pin are urged into direct abutting contact with respect to one another responsive to simultaneous pressing of said first unlocking button and said second unlocking button to facilitate simultaneous movement thereof within said needle cover button slot responsive to subsequent activation of said needle cover button.

11. A hypodermic syringe apparatus according to claim 10 wherein said first pin and said second pin each are square in cross-section to facilitate close abutting contact with respect to one another.

12. A hypodermic syringe apparatus according to claim 1 wherein said needle cover is circular in cross-sectional shape and wherein said needle cover button hole is circular in cross-sectional shape to facilitate movement of said needle cover through said needle cover button hole responsive to activation of said needle cover button.

13. A hypodermic syringe apparatus according to claim 1 wherein said needle cover includes a needle cover tab which is adapted to move along with said needle cover through said needle cover button hole from the retracted position to the deployed position extending around and shielding said needle, said needle cover tab adapted to expand outwardly away from said needle cover responsive to positioning thereof in the deployed position to prevent any return movement of said needle cover from the deployed position toward the retracted position.

14. A hypodermic syringe apparatus according to claim 1 wherein said needle cover button is oriented axially perpendicularly with respect to said needle cover to facilitate control of movement thereof from the retracted position to the deployed position.

15. A hypodermic syringe apparatus according to claim 1 wherein said fluid housing is transparent and said chamber defined therewithin is attached with respect to and in fluid flow communication with respect to said needle channel defined within said needle to facilitate fluid movement therebetween.

16. A hypodermic syringe apparatus according to claim 1 wherein said needle cover button defines a needle cover button channel therein immediately adjacent to and in fluid flow communication with said needle cover button hole defined therein, said needle cover button channel defined to receive said needle positioned extending therethrough responsive to said needle cover button being de-activated, said needle cover button hole being movable to a position wherein said needle cover button hole moves to a position receiving and surrounding said needle extending therethrough responsive to activation of said needle cover button.

17. A hypodermic syringe apparatus according to claim 16 wherein said needle cover button channel is generally rectangular in shape.

18. A hypodermic syringe apparatus according to claim 1 further comprising a gripping means extending around said bushing to facilitate manual operation of the hypodermic syringe apparatus, said gripping means defining a grip aperture extending therethrough which is positioned in registration with respect to said bushing aperture means.

19. A hypodermic syringe apparatus according to claim 18 wherein said gripping means comprises:

a rear gripping section extending around said bushing to facilitate manual operation of the apparatus; and a front gripping section positioned extending around said bushing to facilitate manual operation of the apparatus at a position spatially disposed from said rear gripping section and closer to said needle than said rear gripping section.

20. A hypodermic syringe apparatus according to claim 19 wherein said grip aperture is defined within said front gripping section to facilitate receiving of said needle cover button therein.

21. A hypodermic syringe apparatus according to claim 18 wherein said gripping means is made of thermoplastic.

\* \* \* \* \*